United States Patent [19]

Hassall et al.

[11] 4,307,094

[45] Dec. 22, 1981

[54] TRIAZOLOPYRIDAZINE DERIVATIVES

[75] Inventors: Cedric H. Hassall, Hatfield; Christopher J. Moody, Stevenage, both of England

[73] Assignee: Hoffmann-La Roche Inc., Nutley, N.J.

[21] Appl. No.: 169,571

[22] Filed: Jul. 17, 1980

[30] Foreign Application Priority Data

Jul. 23, 1979 [GB] United Kingdom ............... 25576/79
Apr. 22, 1980 [GB] United Kingdom ............... 13203/80

[51] Int. Cl.³ .................... C07D 487/04; A61K 31/50
[52] U.S. Cl. ...................................... 424/250; 544/236
[58] Field of Search ......................... 424/250; 544/236

[56] References Cited

U.S. PATENT DOCUMENTS 3,621,099  11/1971  Jacobson et al.
3,663,564   5/1972  Jacobson et al.

FOREIGN PATENT DOCUMENTS 1492457  11/1977  United Kingdom.

OTHER PUBLICATIONS

Davies et al., J. C. S., Perkins I, 2390, (1976).

Primary Examiner—Mark L. Berch
Attorney, Agent, or Firm—Jon S. Saxe; Bernard S. Leon; James H. Callwood

[57] ABSTRACT

The present disclosure is directed to 1-substituted or unsubstituted lower alkylene, 5-carboxy, alkanoyloxy or carbamoyloxy triazolopyridazine derivatives, salts of the acids and pharmaceutically-acceptable bases thereof. The triazolopyridazine derivatives provided by the present invention are useful as angiotensin-related antihypertensive agents.

32 Claims, No Drawings

TRIAZOLOPYRIDAZINE DERIVATIVES

BACKGROUND OF THE INVENTION

The present invention relates to triazolopyridazine derivatives. More particularly, the invention is concerned with triazolopyridazine derivatives; a process for the manufacture thereof and pharmaceutical preparations containing same.

SUMMARY OF THE INVENTION

The triazolopyridazine derivatives provided by the present invention are compounds of the general formula

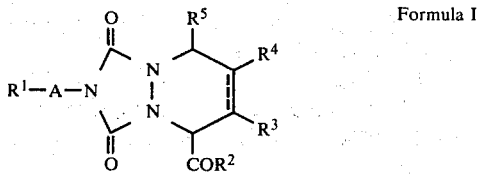

Formula I wherein A is methylene, ethylene or propylene which may be substituted by lower alkyl; $R^1$ is halogen, carboxyl, lower alkoxycarbonyl, aminocarbonyl, hydroxyaminocarbonyl, hydrazinocarbonyl, mercapto, lower alkanoylthio or aryl-lower alkylthio; $R^2$ is hydroxy, lower alkoxy or amino; $R^3$ and $R^4$ each is hydrogen or halogen or $R^3$ is hydrogen and $R^4$ is hydroxy; $R^5$ is hydrogen, lower alkyl, aryl, carboxy, lower alkoxycarbonyl or aminocarbonyl; and the broken line denotes an optional carbon-carbon bond which can be present only when $R^3$ and $R^4$ each is hydrogen, and salts of the acids of formula I with pharmaceutically-acceptable bases.

DETAILED DESCRIPTION OF THE INVENTION

As used in this specification, the term "lower alkyl" alone or in combination means straight- or branched-chain saturated hydrocarbon groups which preferably contain from 1 to 6 carbon atoms (e.g., methyl, ethyl, propyl, isopropyl, butyl, tert.butyl, pentyl and hexyl). The term "lower alkoxy" alone or in combination means a straight- or branched-chain lower alkyl group attached to the remainder of the molecule by oxygen. Exemplary of lower alkoxy are methoxy, ethoxy, propoxy, isopropoxy, etc. Examples of lower alkoxycarbonyl groups are methoxycarbonyl, ethoxycarbonyl and the like. The lower alkanoyl moiety of a lower alkanoylthio group is derived from a straight- or branched-chain alkanoic acid which preferably contains up to 6 carbon atoms such as acetic acid, propionic acid, butyric acid, isobutyric acid, valeric acid, pivalic acid, etc., examples of lower alkanoylthio groups thus being acetylthio, propionylthio, etc. The term "aryl" alone or in combination means an organic radical derived by the removal of one atom (e.g., phenyl) which can be substituted or unsubstituted with one or more substituents such as halogen, lower alkyl, lower alkoxy, trifluoromethyl, lower alkylthio and the like. An example of an aryl-lower alkylthio group is the benzylthio group. The term "halogen" means fluorine, chlorine, bromine or iodine.

A preferred class of components of formula I comprises those in which A is ethylene. Other preferred compounds of formula I are those in which $R^1$ is carboxyl, hydroxyaminocarbonyl or mercapto as well as those in which $R^2$ is hydroxy. Compounds of formula I in which a double-bond is present in the 6,7-position are also preferred. As regards $R^5$, this preferably is hydrogen or aryl, expecially phenyl.

Examples of compounds of formula I hereinbefore are:

5-carboxy-2,3,5,8-tetrahydro-1,3-dioxo-1H-1,2,4-triazolo[1,2-a]pyridazine-2-acetic acid,
5-carboxy-2,3,5,8-tetrahydro-1,3-dioxo-1H-1,2,4-triazolo[1,2-a]pyridazine-2-butyric acid,
2-(2-chloroethyl)-2,3,5,8-tetrahydro-1,3-dioxo-1H-1,2,4-triazolo[1,2-a]pyridazine-5-carboxylic acid,
2-(3-chloropropyl)-2,3,5,8-tetrahydro-1,3-dioxo-1H-1,2,4-triazolo[1,2-a]pyridazine-5-carboxylic acid,
methyl 5-carboxy-2,3,5,8-tetrahydro-1,3-dioxo-1H-1,2,4-triazolo[1,2-a]pyridazine-2-propionate,
5-carboxy-2,3,5,8-tetrahydro-8-methyl-1,3-dioxo-1H-1,2,4-triazolo[1,2-a]pyridazine-2-propionic acid,
2-(2-benzylthioethyl)-2,3,5,8-tetrahydro-1,3-dioxo-1H-1,2,4-triazolo[1,2-a]pyridazine-5-carboxylic acid,
methyl 2-acetylthiomethyl-2,3,5,8-tetrahydro-1,3-dioxo-1H-1,2,4-triazolo[1,2-a]-pyridazine-5-carboxylate,
tert.butyl 2-(2-acetylthioethyl)-2,3,5,8-tetrahydro-1,3-dioxo-1H-1,2,4-triazolo-[1,2-a]pyridazine-5-carboxylate,
tert.butyl 2-[2-(N-hydroxycarbamoyl)ethyl]-2,3,5,8-tetrahydro-1,3-dioxo-1H-1,2,4-triazolo[1,2-a]pyridazine-5-carboxylic acid,
2-(2-carbamoylethyl)-2,3,5,8-tetrahydro-1,3-dioxo-1H-1,2,4-triazolo[1,2-a]pyridazine-5-carboxylic acid,
5-carbamoyl-2,3,5,8-tetrahydro-1,3-dioxo-1H-1,2,4-triazolo[1,2-a]pyridazine-2-propionamide,
2-[(2-hydrazinocarbonyl)ethyl]-2,3,5,8-tetrahydro-1,3-dioxo-1H-1,2,4-triazolo[1,2-a]pyridazine-5-carboxylic acid,
5-carboxy-2,3,5,6,7,8-hexahydro-1,3-dioxo-1H-1,2,4-triazolo[1,2-a]pyridazine-2-acetic acid,
5-carboxy-2,3,5,6,7,8-hexahydro-1,3-dioxo-1H-1,2,4-triazolo[1,2-a]pyridazine-2-propionic acid.
5-carboxy-2,3,5,6,7,8-hexahydro-1,3-dioxo-1H-1,2,4-triazolo[1,2-a]pyridazine-2-butyric acid,
methyl 2,3,5,6,7,8-hexahydro-1,3-dioxo-1H-1,2,4-triazolo[1,2-a]pyridazine-2-propionate,
2-(2-chloroethyl)-2,3,5,6,7,8-hexahydro-1,3-dioxo-1H-1,2,4-triazolo[1,2-a]pyridazine-5-carboxylic acid,
benzyl 5-methoxycarbonyl-2,3,5,8-tetrahydro-1,3-dioxo-1H-1,2,4-triazolo[1,2-a]-pyridazine-2-acetate,
methyl 2-(2-chloroethyl)-2,3,5,6,7,8-hexahydro-1,3-dioxo-1H-1,2,4-triazolo[1,2-a]-pyridazine-5-carboxylate,
methyl 2-chloromethyl-2,3,5,8-tetrahydro-1,3-dioxo-1H-1,2,4-triazolo[1,2-a]-pyridazine-5-carboxylate,
6,7-dibromo-5-carboxy-hexahydro-1,3-dioxo-1H-1,2,4-triazolo[1,2-a]pyridazine-2-propionic acid,
5-carboxy-hexahydro-7-hydroxy-1,3-dioxo-1H-1,2,4-triazolo[1,2-a]pyridazine-2-propionic acid,
tert.butyl 2-(2-chloroethyl)-2,3,5,8-tetrahydro-1,3-dioxo-1H-1,2,4-triazolo[1,2-a]-pyridazine-5-carboxylate, methyl 2,3,5,8-tetrahydro-5-tert.butoxycarbonyl-1,3-dioxo-1H-1,2,4-triazolo-[1,2-a]pyridazine-2-propionate and methyl 2,3,5,8-tetrahydro-5-methoxycarbonyl-1,3-dioxo-1H-1,2,4-triazolo[1,2-a]-pyridazine-2-propionate.

Further examples of preferred compounds of formula I hereinbefore are:

dimethyl 2-(2-methoxycarbonylethyl)-2,3,5,8-tetrahydro-1,3-dioxo-1H-1,2,4-triazolo-[1,2-a]pyridazine-5,8-dicarboxylate, 2-(2-carboxyethyl)-2,3,5,8-tetrahydro-1,3-dioxo-1H-1,2,4-triazolo[1,2-a]pyridazine-5,8-dicarboxylic acid, cis-2-(2-chloroethyl)-2,3,5,8-tetrahydro-1,3-dioxo-8-phenyl-1H-1,2,4-triazolo[1,2-a]pyridazine-5-carboxylic acid, ethyl cis-2-(2-chloroethyl)-2,3,5,8-tetrahydro-1,3-dioxo-8-phenyl-1H-1,2,4-triazolo-[1,2-a]pyridazine-5-carboxylate, ethyl trans-2-(2-chloroethyl)-2,3,5,8-tetrahydro-1,3-dioxo-8-phenyl-1H-1,2,4-triazolo-[1,2-a]pyridazine-5-carboxylate, trans-2-(2-chloroethyl)-2,3,5,8-tetrahydro-1,3-dioxo-8-phenyl-1H-1,2,4-triazolo-[1,2-a]pyridazine-5-carboxylic acid, methyl trans-2-(2-acetylthioethyl)-2,3,5,8-tetrahydro-1,3-dioxo-8-phenyl-1H-1,2,4-triazolo[1,2-a]pyridazine-5-carboxylate, methyl cis-2-(2-acetylthioethyl)-2,3,5,8-tetrahydro-1,3-dioxo-8-phenyl-1H-1,2,4-triazolo[1,2-a]pyridazine-5-carboxylate, trans-2,3,5,8-tetrahydro-2-(2-mercaptoethyl)-1,3-dioxo-8-phenyl-1H-1,2,4-triazolo-[1,2-a]pyridazine-5-carboxylic acid, ethyl 2,3,5,6,7,8-hexahydro-2-(2-chloroethyl)-1,3-dioxo-8-phenyl-1H-1,2,4-triazolo-[1,2-a]pyridazine-5-carboxylate, ethyl 2,3,5,6,7,8-hexahydro-2-(2-acetylthioethyl)-1,3-dioxo-8-phenyl-1H-1,2,4-triazolo-[1,2-a]pyridazine-5-carboxylate, 2,3,5,6,7,8-hexahydro-2-(2-mercaptoethyl)-1,3-dioxo-8-phenyl-1H-1,2,4-triazolo-[1,2-a]pyridazine-5-carboxylic acid, ethyl 2-(2-chloroethyl)-2,3,5,8-tetrahydro-8-(4-chlorophenyl)-1,3-dioxo-1H-1,2,4-triazolo[1,2-a]pyridazine-5-carboxylate, ethyl 2-(2-chloroethyl)-2,3,5,6,7,8-hexahydro-8-(4-chlorophenyl)-1,3-dioxo-1H-1,2,4-triazolo[1,2-a]pyridazine-5-carboxylate, ethyl 2-(2-acetylthioethyl)-2,3,5,6,7,8-hexahydro-8-(4-chlorophenyl)-1,3-dioxo-1H-1,2,4-triazolo[1,2-a]pyridazine-5-carboxylate, 8-(4-chlorophenyl)-2,3,5,6,7,8-hexahydro-2-(2-mercaptoethyl)-1,3-dioxo-1H-1,2,4-triazolo[1,2-a]pyridazine-5-carboxylic acid, ethyl cis-2-(2-chloroethyl)-2,3,5,8-tetrahydro-8-(4-methoxyphenyl)-1,3-dioxo-1H-1,2,4-triazolo[1,2-a]pyridazine-5-carboxylate, cis 2-(2-chloroethyl)-2,3,5,8-tetrahydro-8-(4-methoxyphenyl)-1,3-dioxo-1H-1,2,4-triazolo[1,2-a]pyridazine-5-carboxylic acid, ethyl cis-2-(2-chloroethyl)-2,3,5,8-tetrahydro-8-(4-nitrophenyl)-1,3-dioxo-1H-1,2,4-triazolo[1,2-a]pyridazine-5-carboxylate, cis-2-(2-chloroethyl)-2,3,5,8-tetrahydro-8-(4-nitrophenyl)-1,3-dioxo-1H-1,2,4-triazolo-[1,2-a]pyridazine-5-carboxylic acid, ethyl 2-chloromethyl-2,3,5,8-tetrahydro-1,3-dioxo-8-phenyl-1H-1,2,4-triazolo[1,2-a]pyridazine-5-carboxylate, ethyl 2-chloromethyl-2,3,5,6,7,8-hexahydro-1,3-dioxo-8-phenyl-1H-1,2,4-triazolo-[1,2-a]pyridazine-5-carboxylate, ethyl 2-acetylthiomethyl-2,3,5,6,7,8-hexahydro-1,3-dioxo-8-phenyl-1H-1,2,4-triazolo-[1,2-a]pyridazine-5-carboxylate, 2,3,5,6,7,8-hexahydro-2-mercaptomethyl-1,3-dioxo-8-phenyl-1H-1,2,4-triazolo[1,2-a]pyridazine-5-carboxylic acid, 2,3,5,8-tetrahydro-2-mercaptomethyl-1,3-dioxo-1H-1,2,4-triazolo[1,2-a]pyridazine-5-carboxylic acid, methyl 2,3,5,8-tetrahydro-2-(3-acetylthiopropyl)-1,3-dioxo-1H-1,2,4-triazolo[1,2-a]pyridazine-5-carboxylate, 2,3,5,8-tetrahydro-2-(3-mercaptopropyl)-1,3-dioxo-1H-1,2,4-triazolo[1,2-a]pyridazine-5-carboxylic acid, methyl 2-chloromethyl-2,3,5,6,7,8-hexahydro-1,3-dioxo-1H-1,2,4-triazolo[1,2-a]-pyridazine-5-carboxylate, methyl 2-acetylthiomethyl-2,3,5,6,7,8-hexahydro-1,3-dioxo-1H-1,2,4-triazolo[1,2-a]pyridazine-5-carboxylate, and 2,3,5,6,7,8-hexahydro-2-mercaptomethyl-1,3-dioxo-1H-1,2,4-triazolo[1,2-a]pyridazine-5-carboxylic acid.

Particularly-preferred compounds of formula I hereinbefore are:

5-carboxy-2,3,5,8-tetrahydro-1,3-dioxo-1H-1,2,4-triazolo[1,2-a]pyridazine-2-propionic acid, 5-carboxy-2,3,5,8-tetrahydro-8-phenyl-1,3-dioxo-1H-1,2,4-triazolo[1,2-a]pyridazine-2-propionic acid, 2,3,5,8-tetrahydro-2-(2-mercaptoethyl)-1,3-dioxo-1H-1,2,4-triazolo[1,2-a]pyridazine-5-carboxylic acid, and 2-[2-(N-hydroxycarbamoyl)ethyl]-2,3,5,8-tetrahydro-1,3-dioxo-1H-1,2,4-triazolo[1,2-a]pyridazine-5-carboxylic acid.

According to the process provided by the present invention, the triazolopyridazine derivatives aforesaid (i.e., the compounds for formula I and salts of the acids of formula I with pharmaceutically-acceptable bases) are manufactured by (a) for the manufacture of a compound of formula I in which $R^1$ is halogen, carboxyl or lower alkoxycarbonyl, a double bond is present in the 6,7-position; and A, $R^2$ and $R^5$ are as above, reacting a compound of the general formula

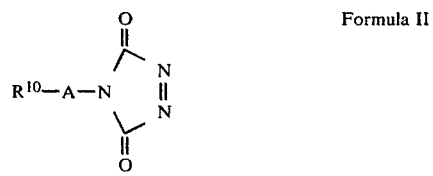

Formula II wherein $R^{10}$ is halogen, carboxyl or lower alkoxycarbonyl, with a compound of the general formula

Formula III wherein $R^2$ and $R^5$ are as above, or (b) for the manufacture of a compound of formula I in which $R^1$ is lower alkanoylthio or aryl-lower alkylthio; and A, $R^2$, $R^3$, $R^4$, $R^5$ and the broken line are as above, reacting a compound of the general formula

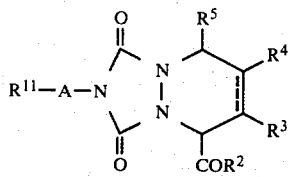

Formula Ia wherein A, $R^2$, $R^3$, $R^4$, $R^5$ and the broken line are as above; and $R^{11}$ is halogen, with a compound of the general formula Formula IV

$R^6$—SH wherein $R^6$ is lower alkanoyl or aryl-lower alkyl, or (c) for the manufacture of a compound of formula I in which $R^1$ is mercapto; and A, $R^2$, $R^3$, $R^4$, $R^5$ and the broken line are as above, cleaving off the group denoted by $R^6$ in a compound of the general formula

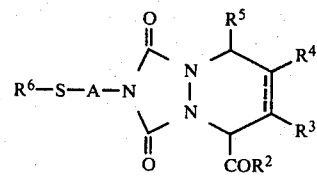

Formula Ib wherein A, $R^2$, $R^5$, $R^6$ and the broken line are as above, or (d) for the manufacture of a compound of formula I in which $R^1$ is aminocarbonyl, hydroxyaminocarbonyl or hydrazinocarbonyl; and A, $R^2$, $R^3$, $R^4$, $R^5$ and the broken line are as above, reacting a compound of the general formula

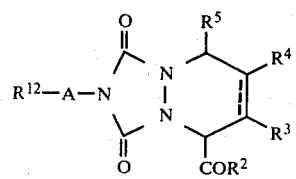

Formula Ic wherein A, $R^2$, $R^3$, $R^4$, $R^5$ are the broken line are as above; and $R^{12}$ is lower alkoxycarbonyl, with a compounder of the general formula Formula V

Y—NH$_2$ wherein Y is hydrogen, hydroxy or an amino group, or (e) for the manufacture of a compound of formula I in which $R^1$ is halogen, carboxyl, lower alkoxycarbonyl, aminocarbonyl, hydroxyaminocarbonyl or hydrazinocarbonyl; $R^3$ and $R^4$ each is hydrogen, a single bond is present in the 6,7-position; and A, $R^2$ and $R^5$ are as above, catalytically hydrogenating a corresponding compound of formula I in which a double bond is present in the 6,7-position, or (f) reacting a compound of the general formula

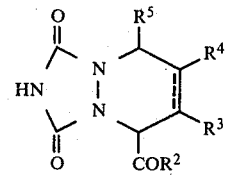

Formula VI wherein $R^2$, $R^3$, $R^4$, $R^5$ and the broken line are as above, with a compound of the general formula Formula VII

$R^1$—A—X wherein $R^1$ and A are as above; and X is a leaving atom or group, or (g) for the manufacture of a compound of formula I in which A is methylene; $R^1$ is halogen; $R^2$ is lower alkoxy or amino; and $R^2$, $R^3$, $R^4$, $R^5$ and the broken line are as above, appropriately halogenating a compound of the general formula

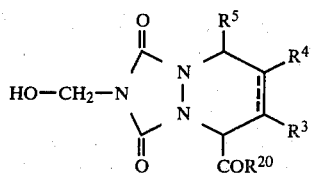

Formula VIII wherein $R^3$, $R^4$, $R^5$ and the broken line are as above; and $R^{20}$ is lower alkoxy or amino, or (h) for the manufacture of a compound of formula I in which $R^3$ and $R^4$ each is halogen, a single bond is present in the 6,7-position; and A, $R^1$, $R^2$ and $R^5$ are as above, treating a compound of formula I in which a double bond is present in the 6,7-position with a hydrogen halide in the presence of hydrogen peroxide, or (i) for the manufacture of a compound of formula I in which $R^3$ is hydrogen; $R^4$ is hydroxy, a single bond is present in the 6,7-position; and A, $R^1$, $R^2$ and $R^5$ are as above, hydrolyzing a compound of the general formula

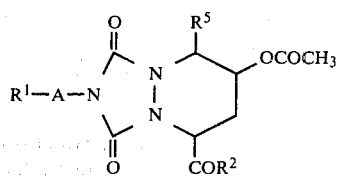

Formula XI wherein A, $R^1$, $R^2$ and $R^5$ are as above, or (j) for the manufacture of a compound of formula I in which $R^1$ is lower alkoxycarbonyl; and/or $R^2$ is lower alkoxy, esterifying a corresponding compound of formula I in which $R^1$ is carboxyl and/or $R^2$ is hydroxy, or (k) for the manufacture of a compound of formula I in which $R^1$ is carboxyl; and/or $R^2$ is hydroxy, treating a corresponding compound of formula I in which $R^1$ is lower alkoxycarbonyl and/or $R^2$ is lower alkoxy, with an acid or a base, or (l) for the manufacture of a salt of an acid of formula I, converting an acid of formula I into a salt with a pharmaceutically-acceptable base.

The reaction of a compound of formula II with a compound of formula III in accordance with embodiment (a) of the present process is conveniently carried out in the presence of an inert organic solvent. Suitable inert organic solvents which can be used include aromatic hydrocarbons (e.g., benzene, toluene, etc.), chlorinated hydrocarbons (e.g., dichloromethane, chloroform, chlorobenzene, etc.), ethers (e.g., diethyl ether, dioxan, etc.), ethyl acetate and the like. Dioxan is the preferred inert organic solvent. The reaction can be carried out at a temperature between about $-10°$ C. and the boiling point of the reaction mixture, preferably at about room temperature. In a preferred aspect of this embodiment, the compound of formula II is reacted with the compound of formula III in situ; that is to say, without isolation from the medium in which it is prepared.

The reaction of a compound of formula Ia with a compound of formula IV in accordance with embodiment (b) of the present process is preferably carried out in the presence of a base and in an inert solvent. Included among the bases which can be used are alkali metal hydroxides (e.g., sodium hydroxide and potassium hydroxide), alkali metal hydrides (e.g., sodium hydride and potassium hydride), alkali metal alkoxides (e.g., sodium methoxide, sodium ethoxide, etc.) and alkali metal carbonates (e.g., sodium carbonate and potassium carbonate). When $R^6$ in the compound of formula IV is lower alkanoyl, suitable solvents are di(-lower alkyl) ketones (e.g., acetone and dimethylformamide or, when an alkali metal carbonate is used as the base, a mixture of water and a chlorinated hydrocarbon (e.g., methylene chloride) or a mixture of water and ethyl acetate. When $R^6$ in the compound of formula IV is aryl-lower alkyl, suitable solvents are water, dimethylformamide, etc. It may be expedient to use a compound of formula III in which $R^6$ is lower alkanoyl in the form of an alkali metal salt (e.g., the potassium salt) and to carry out the reaction in the presence of a catalytic amount of an alkali metal iodide (e.g., potassium iodide). The reaction of a compound of formula Ia with a compound of formula IV can be carried out at a temperature of from about $10°$ C. to the reflux temperature of the reaction mixture. It is preferred to carry out the reaction at the reflux temperature of the reaction mixture.

The cleavage of the group denoted by $R^6$ in a compound of formula Ib in accordance with embodiment (c) of the present process can be carried out in a manner known per se; the particular cleavage method used depending on the nature of $R^6$. For example, when $R^6$ is lower alkanoyl, the cleavage can be carried out using an aqueous alkali metal hydroxide (e.g., aqueous sodium hydroxide or aqueous potassium hydroxide), aqueous ammonia, a lower alkanol (e.g., methanol) in the presence of the corresponding alkali metal lower alkoxide (e.g., sodium methoxide) or a mineral acid such as hydrochloric acid at about $100°$ C. The use of aqueous ammonia is preferred. Again, for example, when $R^6$ is aryl-lower alkyl, the cleavage can be carried out using sodium in liquid ammonia.

In accordance with embodiment (d) of the present process, a compound of formula Ic is reacted with a compound of formula V, namely with ammonia, hydroxylamine or hydrazine. The reaction is expediently carried out in an inert organic solvent such as a lower alkanol, especially methanol. Although the reaction can be carried out at a temperature between about $0°$ C. and the reflux temperature of the reaction mixture, it is preferably carried out at about room temperature. The hydroxylamine can be used in the form of an acid addition salt (e.g., the hydrochloride), in which case a suitable base (e.g., an alkali metal hydroxide, particularly potassium hydroxide) is included in the reaction mixture.

In accordance with embodiment (e) of the present process, a compound of formula I in which a double bond is present in the 6,7-position is catalytically hydrogenated. Suitable catalysts which may be used are noble metal catalysts such as, for example, palladium, platinum, ruthenium, rhodium and Raney nickel. The catalyst may be supported on a suitable carrier material (e.g., palladium-on-carbon, rhodium-on-alumina, etc). The catalytic hydrogenation can be carried out in a conventional inert organic solvent such as, for example, an aromatic hydrocarbon (e.g., benzene, toluene, xylene, etc.), a lower alkanol (e.g., methanol, ethanol, etc.) or an ether (e.g., dioxan, etc.) The catalytic hydrogenation is advantageously carried out at room temperature and at atmospheric pressure.

The leaving atom or group denoted by X in a compound of formula VII can be any conventional leaving atom or group; for example, a chlorine, bromine or iodine atom or a lower alkylsulphonyloxy group (e.g., mesyloxy) or an arylsulphonyloxy group (e.g., tosyloxy). Preferably, X is bromine.

The reaction of a compound of formula VI with a compound of formula VII in accordance with embodiment (f) of the present process is conveniently carried out in the presence of a base and in an inert organic solvent. For example, the reaction can be carried out using alkali metal lower alkoxide such as potassium tert.butoxide in the corresponding lower alkanol such as tert.butanol or using an alkali metal carbonate such as potassium carbonate or an alkali metal hydride such as sodium hydride in dimethylformamide. The temperature at which this reaction is carried out is not critical, but the reflux temperature of the reaction mixture is preferred.

The halogenation of a compound of formula VIII in accordance with embodiment (g) of the present process can be carried out in a manner known per se. Preferred halogenating agents which can be used are phosphorus trichloride, phosphorus pentachloride, phosphorus tribromide and thionyl chloride. A chlorinating agent, particularly phosphorus pentachloride, is especially preferred. The halogenation is expediently carried out in the presence of an ether (e.g., diethyl ether, etc.) and at a temperature between about $-10°$ C. and $+30°$ C., especially at about room temperature.

According to embodiment (h) of the present process, a compound of formula I in which a double bond is present in the 6,7-position is treated with a hydrogen halide in the presence of hydrogen peroxide. In this embodiment, the hydrogen halide is preferably used in aqueous solution with aqueous hydrogen bromide being preferred. This treatment is advantageously carried out at a temperature between about −10° C. and +10° C., preferably at about +5° C.

According to embodiment (i) of the present process, a compound of formula XI is hydrolyzed. The hydrolysis can be carried out using an acid or a base in a manner known per se; for example, using hydrochloric acid at an elevated temperature (e.g., 100° C.).

The esterification of an acid of formula I in which $R^1$ is carboxyl and/or $R^2$ is hydroxy, to give an ester of formula I in which $R^1$ is lower alkoxycarbonyl and/or $R^2$ is lower alkoxy, in accordance with embodiment (j) of the present process can be carried out in a manner known per se. For example, the esterification can be carried out by reacting an acid of formula I with a lower alkanol (e.g., methanol, ethanol, etc.) in the presence of an appropriate acid (e.g., a mineral acid such as hydrochloric acid) or with a suitable diazoalkane (e.g., diazomethane). Alternatively, a carboxylic acid of formula I can firstly be converted in a manner known per se (e.g., by treatment with a chlorinating agent such as thionyl chloride, phosphorus trichloride or phosphorus pentachloride) into a corresponding acid chloride which is then reacted likewise in a manner known per se with a lower alkanol. A tert.butyl ester can also be obtained by reacting an acid of formula I with isobutene in the presence of sulphuric acid.

In accordance with embodiment (k) of the present process, an ester of formula I in which $R^1$ is lower alkoxycarbonyl and/or $R^2$ is lower alkoxy is converted into an acid of formula I in which $R^1$ is carboxyl and/or $R^2$ is hydroxy. The embodiment can be carried out in a manner known per se; for example, by treatment with aqueous alkali metal hydroxide such as sodium hydroxide or potassium hydroxide or an aqueous mineral acid such as hydrochloric acid, conveniently at a temperature between room temperature and the boiling point of the mixture, or, when the ester is a tert.butyl ester, by treatment with anhydrous acid.

Acids of formula I can be converted into salts with pharmaceutically-acceptable bases in accordance with embodiment (l) of the present process. Thus, for example, acids of formula I can be converted into salts by treatment with alkali metal hydroxides (e.g., sodium hydroxide and potassium hydroxide), alkaline earth metal hydroxides (e.g., calcium hydroxide and magnesium hydroxide), organic bases (e.g., dicyclohexylamine, etc.), basic amino acids (e.g., lysine and arginine), etc.

It will be appreciated that the compounds of formula I hereinbefore can occur in racemic or optically-active form and that the present invention includes not only the racemates but also the optical enantiomers. A racemate can be resolved into the optical enantiomers according to conventional methods; for example, by chromatography or by fractional crystallization of salts formed with an optically-active base such as α-methylbenzylamine.

The starting materials of formula II hereinbefore can be prepared by first reacting an isocyanate of the general formula Formula XII

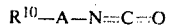

wherein A and $R^{10}$ are as above, with a lower alkoxycarbonylhydrazide such as ethoxycarbonylhydrazide.

The reaction of an isocyanate of formula XII with a lower alkoxycarbonylhydrazide is conveniently carried out in an inert organic solvent (e.g., an aromatic hydrocarbon such as benzene, toluene, etc.) and at room temperature.

The foregoing reaction yields a semicarbazide of the general formula

Formula XIII

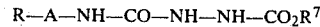

wherein R and A are as above; and $R^7$ is lower alkyl, which is then cyclized to give a compound of the general formula

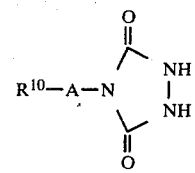

Formula XIV wherein A and $R^{10}$ are as above.

The cyclization of a semicarbazide of formula XIII to give a compound of formula XIV can be carried out by treatment with an alkali metal hydroxide such as sodium hydroxide or, preferably, potassium hydroxide, at a temperature between about 20° C. and 100° C., preferably at about 100° C., followed by acidification (e.g., with a mineral acid such as hydrochloric acid or with an acidic ion-exchange resin) and, where required, reesterification in a manner known per se (e.g., using methanolic hydrochloric acid).

Finally, a compound of formula XIV is converted by oxidation into a compound of formula II. Suitable oxidizing agents which can be used include tert.butyl hypochlorite, nitrogen tetroxide, lead tetraacetate and the like. This oxidation is conveniently carried out in one of the solvents mentioned earlier in connection with embodiment (a) of the process and at a temperature between about −10° C. and +30° C., preferably at room temperature. As mentioned earlier, the resulting compound of formula II is preferably used in embodiment (a) of the present process without isolation from the medium in which it is prepared.

The starting materials of formula III hereinbefore are either known compounds or analogues of known compounds which can be prepared in an analogous manner to the known compounds.

The starting materials of formulae IV, V and VII hereinbefore are known compounds.

The starting material of formula VI in which $R^2$ is hydroxy, a double bond is present in the 6,7-position, and $R^5$ is hydrogen is a known compound. The remaining starting materials of formula VI in which a double bond is present in the 6,7-position can be prepared in an analogous manner to the known compound. Starting materials of formula VI in which a single bond is present in the 6,7-position can be prepared from compounds of formula VI in which a double bond is present in the 6,7-position according to embodiments (e), (h) or (i) of the present process.

The starting materials of formula VIII hereinbefore are novel and can be prepared by treating a compound of formula VI with formaldehyde. This treatment is preferably carried out using aqueous formaldehyde and at an elevated temperature, conveniently at about 100° C.

The starting materials of formula XI are novel and can be prepared by reacting a compound of formula I in which a double bond is present in the 6,7-position with mercuric acetate. This reaction is preferably carried out in the presence of an alkali metal acetate such as sodium acetate and in glacial acetic acid, although a mixture of tetrahydrofuran and water or a lower alkanol such as methanol can also be used. This reaction is advantageously carried out at an elevated temperature, suitably at the reflux temperature of the mixture. The mercury formed in this reaction can be removed by physical methods such as decantation, etc. or by treatment with an alkali metal borohydride such as sodium borohydride. This reaction gives a mixture of compounds of the general formulae

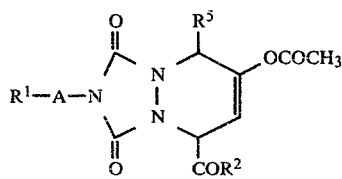

Formula IX and

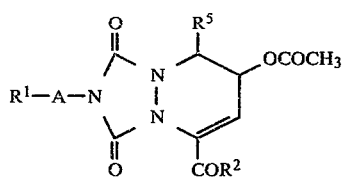

Formula X wherein $A, R^1, R^2$ and $R^5$ are as above.

In the next step, the mixture of compounds of formulae IX and X is catalytically hydrogenated. This catalytic hydrogenation can be carried out in a manner analogous to that described earlier in connection with embodiment (e). However, the use of a rhodium-on-alumina catalyst in glacial acetic acid is preferred. This catalytic hydrogenation gives the compound of the formula XI.

The compounds of formula II, the compounds of formula VI (with the proviso that when a double bond is present in the 6,7-position and $R^2$ is hydroxy, $R^5$ is other than hydrogen), the compounds of formula VIII and the compounds of formula XIV also form part of the present invention.

The triazolopyridazine derivatives provided by the present invention are useful as antihypertensive agents. They inhibit angiotensin converting enzyme (ACE) which brings about the conversion of angiotensin I into angiotesin II and are therefore useful in reducing or alleviating angiostensin-related hypertension.

The activity of the present triazolopyridazine derivatives in inhibiting angiotensin converting enzyme in vitro can be determined by the following test.

The method used is based on the method of Cushman and Cheung (Biochem. Pharmacol., 20, 1637-1648) incorporating the modifications introduced by Hayakari et al. (Anal. Biochem., 84, 361-369). The substrate (hippuryl-histidyl-leucine, 2 mM) is incubated with angiotensin converting enzyme in the presence or absence of various concentrations of test substance in potassium phosphate buffer (pH 8.3; 100 mM) containing sodium chloride (300 mM) for 25 minutes at 37° C. (total value 500 μl). The reaction is terminated by the addition of 3 ml of potassium phosphate buffer (pH 8.3; 200 mM) at 0° C. 2,4,6-trichloro-s-triazine (3%) in 1.5 ml of dioxan is added, and the mixture is agitated until the yellow chromophore has developed fully. The samples are then centrifuged to remove any precipitate which has formed. The yellow chromophore formed by the reaction of the 2,4,6-trichloro-s-triazine with free hippuric acid is measured spectrophotometrically at 382 nm. $IC_{50}$ values are defined as the concentration of test substance which reduces by 50% the cleavage of hippuryl-histidyl-leucine by angiotensin converting enzyme under the aforementioned conditions.

The results obtained in the foregoing test using representative compounds of formula I hereinbefore as the test substance are complied in the following table.

Compound A: 5-carboxy-2,3,5,8-tetrahydro-1,3-dioxo-1H-1,2,4-triazolo[1,2-a]pyridazine-2-propionic acid.
Compound B: 2-(2-carbamoylethyl)-2,3,5,8-tetrahydro-1,3-dioxo-1H-1,2,4-triazolo[1,2-a]-pyridazine-5-carboxylic acid.
Compound C: 2-[2-(N-hydroxycarbamoyl)ethyl]-2,3,5,8-tetrahydro-1,3-dioxo-1H-1,2,4-triazolo[1,2-a]pyridazine-5-carboxylic acid.
Compound D: 2,3,5,8-tetrahydro-2-(2-mercaptoethyl)-1,3-dioxo-1H-1,2,4-triazolo[1,2-a]pyridazine-5-carboxylic acid.

TABLE

| Compound | $IC_{50}(M)$ |
|---|---|
| A | $1.8 \times 10^{-5}$ |
| B | $6.5 \times 10^{-5}$ |
| C | $3.3 \times 10^{-6}$ |
| D | $4.8 \times 10^{-7}$ |

The triazolopyridazine derivatives provided by the present invention can be used as medicaments in the form of pharmaceutical preparations which contain them in association with a compatible pharmaceutical carrier material. This carrier material can be an organic or inorganic carrier material which is suitable for enteral (e.g., oral) or parenteral administration, examples of such carrier materials being water, gelatin, gum arabic, lactose, starch, magnesium stearate, talc, vegetable oils, polyalkyleneglycols, petroleum jelly, etc. The pharmaceutical preparations can be made up in a solid form (e.g., as tablets, dragees, suppositories or capsules) or in a liquid form (e.g., as solutions, suspensions or emulsions). The pharmaceutical preparations may be subjected to standard pharmaceutical operations such as sterilization and/or may contain adjuvants such as preserving, stabilizing, wetting or emulsifying agents, salts for varying the osmotic pressure or buffers. The pharmaceutical preparations may also contain other therapeutically-valuable substances.

The triazolopyridazine derivatives provided by the present invention may be administered to adults in a daily dosage of from about 0.1 mg to 100 mg, preferably about 1 mg to 50 mg, per kilogram body weight. The daily dosage may be administered as a single dose or in divided doses. It will be appreciated that the aforementioned dosage range is given by way of example only and can be varied upwards or downwards depending on factors such as the severity of the indication being treated and the condition of the patient as determined by the attending physician.

The following Examples illustrate the process provided by the present invention:

EXAMPLE 1

(A) A solution of 19.72 g (0.17 mol) of methoxycarbonylmethyl isocyanate in 70 ml of dry toluene was added dropwise at room temperature to a stirred solution of 18.00 g (0.17 mol) of ethoxycarbonylhydrazine in 400 ml of dry toluene. The mixture was stirred at room temperature overnight and filtered. The colourless solid was washed with toluene, dried and recrystallized from ethyl acetate to give 28.54 g (76%) of 1-ethoxycarbonyl-4-methoxycarbonylmethyl-semicarbazide of melting point 116°–121° C.

(B) 27.47 g (0.125 mol) of 1-ethoxycarbonyl-4-methoxycarbonylmethyl-semicarbazide were dissolved in 95 ml (0.38 mol) of 4-M potassium hydroxide solution and heated on a steam-bath for 1.5 hours. The resulting solution was cooled to room temperature, acidified to pH 1 with concentrated hydrochloric acid and evaporated in vacuo to give a colourless solid. This solid was extracted with three 90 ml portions of boiling methanol. The extracts were filtered, combined and added to 400 ml of methanolic hydrogen chloride. The mixture was left to stand at room temperature overnight and then evaporated in vacuo to give a colourless solid. This solid was recrystallized from methanol to give 7.50 g (35%) of methyl 3,5-dioxo-1,2,4-triazolidine-4-acetate of melting point 215°–218° C.

(C) 0.5 g (2.9 mmol) of methyl 3,5-dioxo-1,2,4-triazolidine-4-acetate was stirred at room temperature for 2 hours with 8.7 ml (8.7 mmol) of 1-M sodium hydroxide solution. The resulting solution was acidified with concentrated hydrochloric acid and evaporated to dryness. The solid residue was extracted with hot acetonitrile. The acetonitrile extracts were evaporated and the residual colourless solid was recrystallized from acetonitrile, there being obtained 0.15 g (33%) of 3,5-dioxo-1,2,4-triazolidine-4-acetic acid of melting point 220°–223° C. (from acetonitrile).

(D) 1.69 g (0.011 mol) of 3,5-dioxo-1,2,4-triazolidine-4-acetic acid were suspended in 20 ml of dry dioxan and the suspension was stirred at room temperature under a stream of nitrogen. A solution of 1.32 g (0.012 mol) of tert.butyl hypochlorite in 4 ml of dry dioxan was added dropwise over a period of 15 minutes. Stirring was continued for 45 minutes, the resulting red solution was filtered and the filtrate was evaporated in vacuo to give a red solid. This red solid was dissolved in 30 ml of dioxan and added portionwise to a stirred solution of 1.25 g (0.013 mol) of penta-2,4-dienoic acid in 20 ml of dioxan. The red colour was allowed to fade between the additions. After completion of the addition and when no red colour persisted, the solution was stirred at room temperature for 1 hour and evaporated in vacuo to give a colourless solid. This solid was recrystallized from acetonitrile to give 1.17 g (43%) of 5-carboxy-2,3,5,8-tetrahydro-1,3-dioxo-1H-1,2,4-triazolo-[1,2-a]pyridazine-2-acetic acid of melting point 209°–211° C. (decomposition).

EXAMPLE 2

(A) In a manner analogous to that described in Example 1(A), from 2-methoxycarbonylethyl isocyanate there was obtained in 70% yield 1-ethoxycarbonyl-4-(2-methoxycarbonylethyl)-semicarbazide of melting point 105°–107° C.

(B) In a manner analogous to that described in Example 1(B), from 1-ethoxycarbonyl-4-(2-methoxycarbonylethyl)-semicarbazide there was obtained in 42% yield methyl 3,5-dioxo-1,2,4-triazolidine-4-propionate of melting point 150°–153° C.

(C) In a manner analogous to that described in Example 1(C), from methyl 3,5-dioxo-1,2,4-triazolidine-4-propionate there was obtained 3,5-dioxo-1,2,4-triazolidine-4-pripionic acid of melting point 180°–183° C. (from acetonitrile).

(D) In a manner analogous to that described in Example 1(D), from 3,5-dioxo-1,2,4-triazolidine-4-propionic acid there was obtained in 63% yield 5-carboxy-2,3,5,8-tetrahydro-1,3-dioxo-1H-1,2,4-triazolo[1,2-a]pyridazine-2-propionic acid of melting point 172°–175° C. (from acetonitrile).

EXAMPLE 3

(A) In a manner analogous to that described in Example 1(A), from 3-methoxycarbonylpropyl isocyanate there was obtained in 76% yield 1-ethoxycarbonyl-4-(3-methoxycarbonylpropyl)-semicarbazide of melting point 95°–96° C.

(B) 494 mg (2 mmol) of 1-ethoxycarbonyl-4-(3-methoxycarbonylpropyl)-semicarbazide were dissolved in 1.5 ml (6 mmol) of 4-M potassium hydroxide solution and the resulting solution was heated on a steam-bath for 1 hour. The resulting solution was applied to an ion-exchange column (Dowex 50X-8, H+ form) and eluted with water. The eluate was evaporated in vacuo to give a colourless solid which was recrystallized from acetonitrile to give 120 mg (32%) of 3,5-dioxi-1,2,4-triazolidine-4-butyric acid of melting point 168°–170° C.

(C) In a manner analogous to that described in Example 1(D), from 3,5-dioxo-1,2,4-triazolidine-4-butyric acid there was obtained in 44% yield 5-carboxy-2,3,5,8-tetrahydro-1,3-dioxo-1H-1,2,4-triazolo[1,2-a]pyridazine-2-butyric acid of melting point 130° C. (from acetonitrile).

EXAMPLE 4

(A) In a manner analogous to that described in Example 1(A), from 2-chloroethyl isocyanate there was obtained in 73% yield 4-(2-chloroethyl)-1-ethoxycarbonyl-semicarbazide of melting point 118°–120° C.

(B) 23.9 g (0.114 mol) of 4-(2-chloroethyl)-1-ethoxycarbonyl-semicarbazide and 57 ml (0.228 mol) of 4-M potassium hydroxide solution were stirred together at room temperature for 2 hours. The mixture was diluted with 100 ml of water, applied to an ion-exchange column (Dowex 50X-8, H+ form) and eluted with water. The eluate was evaporated in vacuo to give a colourless solid which was recrystallized from water to give 7.97 g (43%) of 4-(2-chloroethyl)-1,2,4-triazolidine-3,5-dione of melting point 192°–193° C.

(C) In a manner analogous to that described in Example 1(D), from 4-(2-chloroethyl)-1,2,4-triazolidine-3,5-dione there was obtained in 85% yield 2-(2-chloroethyl)-2,3,5,8-tetrahydro-1,3-dioxo-1H-1,2,4-triazolo[1,2-a]pyridazine-5-carboxylic acid of melting point 150°–151° C.

EXAMPLE 5

(A) In a manner analogous to that described in Example 1(A), from 3-chloropropyl isocyanate there was obtained in 78% yield 4-(3-chloropropyl)-1-ethoxycarbonyl-semicarbazide of melting point 105°–106° C.

(B) In a manner analogous to that described in Example 4(B), from 4-(3-chloropropyl)-1-ethoxycarbonyl-semicabazide there was obtained in 14% yield 4-(3-chloropropyl)-1,2,4-triazolidine-3,5-dione of melting point 168°–170° C.

(C) In a manner analogous to that described in Example 1(D), from 4-(3-chloropropyl)-1,2,4-triazolidine-3,5-dione there was obtained 2-(3-chloropropyl)-2,3,5,8-tetrahydro-1,3-dioxo-1H-1,2,4-triazolo[1,2-a]pyridazine-5-carboxylic acid.

EXAMPLE 6

In a manner analogous to that described in Example 1(D), from methyl 3,5-dioxo-1,2,4-triazolidine-4-propionate, prepared as described in Example 2(B), there was obtained in 50% yield methyl 5-carboxy-2,3,5,8-tetrahydro-1,3-dioxo-1H-1,2,4-triazolo[1,2-a]pyridazine-2-propionate of melting point 150°–153° C. (from acetonitrile).

Racemic methyl 5-carboxy-2,3,5,8-tetrahydro-1,3-dioxo-1H-1,2,4-triazolo[1,2-a]pyridazine-2-propionate can be resolved via its α-methylbenzylamine salts to give the (+) enantiomer of melting point 180°–181° C. $[[\alpha]_{365}^{20} = +1184°$ (c=0.5 in methanol)] and the (−) enantiomer of melting point 180°–181° C. $[[\alpha]_{365}^{20} = -1181°$ (c=0.5 in methanol)].

EXAMPLE 7

In a manner analogous to that described in Example 1(D), from 3,5-dioxo-1,2,4-triazolidine-4-propionic acid, prepared as described in Example 2(C) and hexa-2,4-dienoic acid, there was obtained in 76% yield 5-carboxy-2,3,5,8-tetrahydro-8-methyl-1,3-dioxo-1H-1,2,4-triazolo[1,2-a]pyridazine-2-propionic acid of melting point 184°–186° C. (from acetonitrile).

EXAMPLE 8

In a manner analogous to that described in Example 1(D), from 3,5-dioxo-1,2,4-triazolidine-4-propionic acid, prepared as described in Example 2(C), and 5-phenyl-penta-2,4-dienoic acid there was obtained in 23% yield 5-carboxy-2,3,5,8-tetrahydro-8-phenyl-1,3-dioxo-1H-1,2,4-triazolo[1,2-a]pyridazine-2-propionic acid of melting point 177°–178° C. (from acetonitrile).

EXAMPLE 9

1.2 g (0.005 mol) of 2-(2-chloroethyl)-2,3,5,8-tetrahydro-1,3-dioxo-1H-1,2,4-triazolo[1,2-a]pyridazine-5-carboxylic acid were dissolved in 10 ml (0.10 mol) of 1-M sodium hydroxide solution. The solution was treated with 1 ml (0.008 mol) of benzyl mercaptan and the mixture was stirred at 100° C. for 3 hours. The mixture was acidified with concentrated hydrochloric acid and extracted with two 20 ml portions of ethyl acetate. The organic layer was extracted with 50 ml of saturated sodium bicarbonate solution. The aqueous extract was acidified with concentrated hydrochloric acid and re-extracted with two 25 ml portions of ethyl acetate. The organic extracts were dried over magnesium sulphate and evaporated to give 2-(2-benzylthioethyl)-2,3,5,8-tetrahydro-1,3-dioxo-1H-1,2,4-triazolo[1,2-a]pyridazine-5-carboxylic acid in the form of a colourless oil.

The foregoing oil was dissolved in 10 ml of acetonitrile and treated with 2 ml of dicyclohexylamine. A colourless solid precipitated. This solid was filtered off and recrystallized from acetonitrile to give 1.83 g (69%) of the dicyclohexylamine salt of 2-(2-benzylthioethyl)-2,3,5,8-tetrahydro-1,3-dioxo-1H-1,2,4-triazolo[1,2-a]pyridazine-5-carboxylic acid melting at 201°–203° C.

EXAMPLE 10

3.24 g (0.0125 mol) of methyl 2-chloromethyl-2,3,5,8-tetrahydro-1,3-dioxo-1H-1,2,4-triazolo[1,2-a]pyridazine-5-carboxylate and 2.29 g (0.02 mol) of potassium thioacetate were refluxed together in 400 ml of acetone with a catalytic amount of sodium iodide for 19 hours. The acetone was removed by evaporation and the residue was partitioned between 250 ml of ethyl acetate and 200 ml of saturated sodium chloride solution. The organic layer was separated, dried over magnesium sulphate and evaporated to give a yellow oil. This oil was chromatographed on silica gel using chloroform/ethyl acetate (1:1) for the elution to give 2.19 g (59%) of methyl 2-acetylthiomethyl-2,3,5,8-tetrahydro-1,3-dioxo-1H-1,2,4-triazolo[1,2-a]pyridazine-5-carboxylate in the form of a colourless solid of melting point 110°–111° C. (from chloroform/hexane).

EXAMPLE 11

In a manner analogous to that described in Example 10, from tert.butyl 2-(2-chloroethyl)-2,3,5,8-tetrahydro-1,3-dioxo-1H-1,2,4-triazolo[1,2-a]pyridazine-5-carboxylate and potassium acetate there was obtained tert.butyl 2-(2-acetylthioethyl)-2,3,5,8-tetrahydro-1,3-dioxo-1H-1,2,4-triazolo[1,2-a]pyridazine-5-carboxylate of melting point 102°–103° C.

EXAMPLE 12

1.75 g (0.005 mol) of tert.butyl 2-(2-acetylthioethyl)-2,3,5,8-tetrahydro-1,3-dioxo-1H-1,2,4-triazolo-[1,2-a]pyridazine-5-carboxylate were dissolved in 20 ml of trifluoroacetic acid. After 1 hour, the trifluoroacetic acid was removed by evaporation to give 2-(2-acetylthioethyl)-2,3,5,8-tetrahydro-1,3-dioxo-1H-1,2,4-triazolo[1,2-a]pyridazine-5-carboxylate. This acid was dissolved in 60 ml of water and the solution was treated with 0.88 ammonia solution under a nitrogen atmosphere. The mixture was stirred at room temperature for 1 hour, acidified with concentrated hydrochloric acid, saturated with sodium chloride and extracted with three 150 ml portions of chloroform. The chloroform extracts were dried over magnesium sulphate and evaporated to give a colourless solid. This solid was crystallized from ethyl acetate/hexane to give 0.92 g (73%) of 2,3,5,8-tetrahydro-2-(2-mercaptoethyl)-1,3-dioxo-1H-1,2,4-triazolo[1,2-a]pyridazine-5-carboxylic acid of melting point 156°–158° C.

EXAMPLE 13

5 g (0.0147 mol) of methyl 2,3,5,8-tetrahydro-5-tert.butyloxycarbonyl-1,3-dioxo-1H-1,2,4-triazolo[1,2-a]-pyridazine-2-propionate were dissolved in 30 ml of methanol and the solution obtained was treated with 8.24 g (0.118 mol) of hydroxylamine hydrochloride and 6.41 g (0.118 mol) of potassium hydroxide. The resulting suspension was stirred at room temperature overnight. 4.12 g (0.059 mol) of hydroxylamine hydrochloride and 3.20 g (0.059 mol) of potassium hydroxide were added and the mixture was stirred at room temperature for a further 88 hours. The mixture was evaporated to dryness, the residue was dissolved in 80 ml of water, the solution was made basic with 4-M potassium hydroxide solution and extracted with two 150 ml portions of ether. The aqueous layer was acidified with 1-M sulphuric acid, saturated with sodium chloride and extracted with four 100 ml portions of chloroform. The chloroform extracts were dried over magnesium sulphate and evaporated to give a yellow oil. This oil was crystallized from 100 ml of ether containing a few drops of water to give 3.81 g (76%) of tert.butyl 2-[2-(N-hydroxycarbamoyl)ethyl]-2,3,5,8-tetrahydro-1,3-dioxo-1H-1,2,4-triazolo[1,2-a]pyridazine-5-carboxylic acid of melting point 75°–78° C.

The foregoing ester was dissolved in 35% hydrogen bromide in acetic acid and the solution was left to stand at room temperature for 1 hour. Addition of ether brought about precipitation of the product which was freeze-dried, there being obtained in 80% yield 2-[2-(N-hydroxycarbamoyl)-ethyl]-2,3,5,8-tetrahydro-1,3-dioxo-1H-1,2,4-triazolo-[1,2-a]pyridazine-5-carboxylic acid.

EXAMPLE 14

2.83 g (0.01 mol) of methyl 5-carboxy-2,3,5,8-tetrahydro-1,3-dioxo-1H-1,2,4-triazolo[1,2-a]pyridazine-2-propionate were dissolved in 50 ml of methanol. The solution was saturated with ammonia and stirred for 72 hours. The mixture was evaporated to dryness and the residue was dissolved in water. The aqueous solution was passed through an ion-exchange column (Zerolit 225, H+ form) and the eluate was evaporated to give a colourless solid. This solid was recrystallized from methanol to give 2.26 g (85%) of 2-(2-carbamoylethyl)-2,3,5,8-tetrahydro-1,3-dioxo-1H-1,2,4-triazolo[1,2-a]pyridazine-5-carboxylic acid of melting point 218°–220° C. (decomposition).

In an analogous manner, from methyl 5-methoxycarbonyl-2,3,5,8-tetrahydro-1,3-dioxo-1H-1,2,4-triazolo[1,2-a]-pyridazine-2-propionate and methanolic ammonia there was obtained in 50% yield 5-carbamoyl-2,3,5,8-tetrahydro-1,3-dioxo-1H-1,2,4-triazolo[1,2-a]pyridazine-2-propionamide monohydrate of melting point 240°–243° C. (freeze-dried).

EXAMPLE 15

283 mg (1 mmol) of methyl 5-carboxy-2,3,5,8-tetrahydro-1,3-dioxo-1H-1,2,4-triazolo[1,2-a]pyridazine-2-propionate were dissolved in 5 ml of methanol and the solution was treated with 1.5 ml (25 mmol) of 85% hydrazine hydrate. The mixture was stirred at room temperature for 24 hours. The colourless precipitate was filtered off and recrystallized from methylate spirits to give 50 mg (18%) of 2-[(2-(hydrazinocarbonyl)ethyl]-2,3,5,8-tetrahydro-1,3-dioxo-1H-1,2,4-triazolo[1,2-a]pyridazine-5-carboxylic acid of melting point 165°–170° C. (decomposition).

EXAMPLE 16

0.75 g of 5-carboxy-2,3,5,8-tetrahydro-1,3-dioxo-1H-1,2,4-triazolo[1,2-a]pyridazine-2-acetic acid was dissolved in 50 ml of dioxan and hydrogenated in the presence of 10% palladium-on-charcoal at room temperature for 3 hours. The catalyst was filtered off and the filtrate was evaporated to give a colourless solid. This solid was recrystallized from acetonitrile to give 0.50 g (67%) of 5-carboxy2,3,5,6,7,8-hexahydro-1,3-dioxo-1H-1,2,4-triazolo[1,2-a]pyridazine-2-acetic acid of melting point 224°–226° C. (from acetonitrile).

The following compounds were prepared in an analogous manner:

5-Carboxy-2,3,5,6,7,8-hexahydro-1,3-dioxo-1-1,2,4-triazolo[1,2-a]pyridazine-2-propionic acid of melting point 189°–192° C., 5-carboxy-2,3,5,6,7,8-hexahydro-1,3-dioxo-1H-1,2,4-triazolo[1,2-a]pyridazine-2-butyric acid of melting point 147°–148° C.

methyl 2,3,5,6,7,8-hexahydro-1,3-dioxo-1H-1,2,4-triazolo[1,2-a]pyridazine-2-propionate of melting point 147°–148° C., and 2-(2-chloroethyl)-2,3,5,6,7,8-hexahydro-1,3-dioxo-1H-1,2,4-triazolo[1,2-a]pyridazine-5-carboxylic acid of melting point 151°–152° C.

EXAMPLE 17

7.25 g (0.036 mol) of hexahydro-1,3-dioxo-1H-1,2,4-triazolo[1,2-a]pyridazine-5-carboxylic acid were heated under reflux for 2 hours in 250 ml of methanolic hydrogen chloride. The solvent was removed by evaporation and the residue was crystallized from methanol to give 5.05 g (65%) of methyl hexahydro-1,3-dioxo-1H-1,2,4-triazolo[1,2-a]-pyridazine-5-carboxylate of melting point 215°–216° C.

1.50 g (0.007 mol) of methyl hexahydro-1,3-dioxo-1H-1,2,4-triazolo[1,2-a]pyridazine-5-carboxylate were dissolved in 40 ml of dry tert.butanol. A solution of 0.87 g (0.008 mol) of potassium tert.butoxide in 50 ml of dry tert.butanol was added and the mixture was stirred under reflux and under a nitrogen atmosphere for 4 hours. 1.61 g (0.007 mol) of benzyl bromoacetate were added and the heating was continued for a further 4 hours. The mixture was filtered and the filtrate was evaporated to dryness. The residue was chromatographed on silica gel using chloroform for the elution to give 1.32 g (52%) of benzyl 5-methoxycarbonyl-2,3,5,6,7,8-hexahydro-1,3-dioxo-1H-1,2,4-triazolo[1,2-a]pyridazine-2-acetate of melting point 103°–106° C. (from dichloromethane/hexane).

Alkylation of methyl hexahydro-1,3-dioxo-1H-1,2,4-triazolo[1,2-a]pyridazine-5-carboxylate with 1-bromo-2-chloroethane in a manner analogous to that described in the preceding paragraph gave methyl 2-(2-chloroethyl)-2,3,5,6,7,8-hexahydro-1,3-dioxo-1H-1,2,4-triazolo[1,2-a]pyridazine-5-carboxylate of melting point 94°–95° C.

EXAMPLE 18

In a manner analogous to that described in the first paragraph of Example 17, from 2,3,5,8-tetrahydro-1,3-dioxo-1H-1,2,4-triazolo[1,2-a]pyridazine-5-carboxylic acid and methanolic hydrogen chloride there was obtained in 74% yield methyl 2,3,5,8-tetrahydro-1,3-dioxo-1H-1,2,4-triazolo-[1,2-a]pyridazine-5-carboxylate of melting point 210°–213° C. (from methanol).

7.02 g (0.033 mol) of methyl 2,3,5,8-tetrahydro-1,3-dioxo-1H-1,2,4-triazolo[1,2-a]pyridazine-5-carboxylate and 9 ml of 40% aqueous formaldehyde were heated on a steam-bath for 4.5 hours. The mixture was evaporated in vacuo to give a colourless oil which was crystallized from dichloromethane/hexane, there being obtained 3.97 g (50%) of methyl 2-hydroxymethyl-2,3,5,8-tetrahydro-1,3-dioxo-1H-1,2,4-triazolo[1,2-a]pyridazine-5-carboxylate of melting point 123°–125° C.

Alternatively, methyl 2-hydroxymethyl-2,3,5,8-tetrahydro-1,3-dioxo-1H-1,2,4-triazolo[1,2-a]pyridazine-5-carboxylate can be prepared as follows:

2,3,5,8-Tetrahydro-1,3-dioxo-1H-1,2,4-triazolo[1,2-a]pyridazine-5-carboxylic acid is reacted with formaldehyde in a manner analogous to that described in the preceding paragraph to give in 44% yield 2,3,5,8-tetrahydro-2-hydroxymethyl-1,3-dioxo-1H-1,2,4-triazolo[1,2-a]pyridazine-5-carboxylic acid of melting point 175°–178° C. (from isopropanol). This acid is esterified using diazomethane in ether to give methyl 2-hydroxymethyl-2,3,5,8-tetrahydro-1,3-dioxo-1H-1,2,4-triazolo[1,2-a]pyridazine-5-carboxylate of melting point 123°–125° C.

3.97 g (0.017 mol) of methyl 2-hydroxymethyl-2,3,5,8-tetrahydro-1,3-dioxo-1H-1,2,4-triazolo[1,2-a]pyridazine-5-carboxylate were suspended at 0° C. in 300 ml of dry ether. 3.49 g (0.017 mol) of phosphorus pentachloride were added portionwise and the mixture was stirred at room temperature for 22 hours. The resulting clear solution was evaporated in vacuo and the residue was chromatographed on silica gel using chloroform/ethyl acetate (1:1) for the elution. There were obtained 3.24 g (76%) of methyl 2-chloromethyl-2,3,5,8-tetrahydro-1,3-dioxo-1H-1,2,4-triazolo[1,2-a]pyridazine-5-carboxylate of melting point 164°–165° C.

EXAMPLE 19

23 ml (ca. 0.23 mol) of 30% hydrogen peroxide were added dropwise to a stirred, cold (0° C.) solution of 6.19 g (0.023 mol) of 5-carboxy-2,3,5,8-tetrahydro-1,3-dioxo-1H-1,2,4-triazolo[1,2-a]pyridazine-2-propionic acid in 115 ml of 40% aqueous hydrogen bromide. After stirring at ca 5° C. for 2 hours, the mixture was evaporated to dryness. The residue was crystallized from acetone/ether to give 3.63 g (37%) of 6,7-dibromo-5-carboxy-hexahydro-1,3-dioxo-1H-1,2,4-triazolo[1,2-a]pyridazine-2-propionic acid of melting point 221°–222° C.

EXAMPLE 20

7.14 g (0.024 mol) of methyl 5-methoxycarbonyl-2,3,5,8-tetrahydro-1,3-dioxo-1H-1,2,4-triazolo[1,2-a]pyridazine-2-propionate were treated with 7.63 g (0.024 mol) of mercuric acetate and 3.94 g (0.048 mol) of anhydrous sodium acetate in 60 ml of glacial acetic acid at 100° C. for 5 hours. The resulting solution was decanted from the precipitated mercury and evaporated to dryness. The solid remaining was extracted repeatedly with dichloromethane. The dichloromethane extracts were evaporated to yield 7.8 g (91%) of a mixture of methyl 7-acetoxy-2,3,5,8-tetrahydro-5-methoxycarbonyl-1,3-dioxo-1H-1,2,4-triazolo[1,2-a]pyridazine-2-propionate and methyl 7-acetoxy-2,3,7,8-tetrahydro-5-methoxycarbonyl-1,3-dioxo-1H-1,2,4-triazolo-[1,2-a]pyridazine-2-propionate in the form of a pale yellow oil.

2.8 g (0.0078 mol) of the foregoing mixture of acetates were dissolved in 20 ml of glacial acetic acid and hydrogenated over 400 mg of rhodium-on-alumina. Working-up in the customary manner followed by chromatography on silica gel using chloroform/methanol (95:5) for the elution gave 1.35 g (48%) of methyl 7-acetoxyhexahydro-5-methoxycarbonyl-1,3-dioxo-1H-1,2,4-triazolo[1,2-a]pyridazine-2-propionate in the form of a yellow oil.

The compound obtained according to the preceding paragraph was hydrolyzed in 20 ml of 6-M hydrochloric acid at 100° C. for 1 hour. Evaporation and crystallization of the residue from acetone gave 0.82 g (69%) of 5-carboxy-hexahydro-7-hydroxy-1,3-dioxo-1H-1,2,4-triazolo[1,2-a]pyridazine-2-propionic acid of melting point 182°–183° C.

EXAMPLE 21

(A) 0.1 mol of 2-(2-chloroethyl)-2,3,5,8-tetrahydro-1,3-dioxo-1H-1,2,4-triazolo[1,2-a]pyridazine-5-carboxylic acid was dissolved in 500 ml of dioxan or dichloromethane. 12 ml of concentrated sulphuric acid were added and the mixture was then treated with 500 ml of isobutene. After stirring at room temperature for 4 days, the mixture was diluted with water and extracted with ether. The ether extracts were washed with 10% sodium carbonate solution, dried over magnesium sulphate and evaporated to give tert.butyl 2-(2-chloroethyl)-2,3,5,8-tetrahydro-1,3-dioxo-1H-1,2,4-triazolo[1,2-a]pyridazine-5-carboxylate of melting point 87°–88° C.

(B) 5 mmol of 2-(2-chloroethyl)-2,3,5,8-tetrahydro-1,3-dioxo-1H-1,2,4-triazolo[1,2-a]pyridazine-5-carboxylic acid were suspended in 40 ml of dry ether and the suspension was stirred at room temperature for 3 hours with 1.18 g (5.5 mmol) of phosphorus pentachloride. The mixture was then evaporated to give the acid chloride. The acid chloride was dissolved in 35 ml of tert.butanol and treated with 2 ml (15 mmol) of N,N-dimethylaniline. The mixture was stirred at room temperature overnight and then evaporated. The residue was partitioned between ethyl acetate and 2-M hydrochloric acid. The ethyl acetate phase was separated, washed with saturated sodium chloride solution and then with saturated sodium bicarbonate solution, dried over magnesium sulphate and evaporated to give tert.butyl 2-(2-chloroethyl)-2,3,5,8-tetrahydro-1,3-dioxo-1H-1,2,4-triazolo[1,2-a]pyridazine-5-carboxylate of melting point 87°–88° C.

In an analogous manner to that described in the preceding paragraphs, from methyl 5-carboxy-2,3,5,8-tetrahydro-1,3-dioxo-1H-1,2,4-triazolo[1,2-a]pyridazine-2-propionate there can be obtained methyl 2,3,5,8-tetrahydro-5-tert.butoxycarbonyl-1,3-dioxo-1H-1,2,4-triazolo[1,2-a]pyridazine-2-propionate of melting point 77°–78° C.

(C) In a manner analogous to that described in the first paragraph of Example 17, from 5-carboxy-2,3,5,8-tetrahydro-1,3-dioxo-1H-1,2,4-triazolo[1,2-a]pyridazine-2-propionic acid there was obtained methyl 2,3,5,8-tetrahydro-5-methoxycarbonyl-1,3-dioxo-1H-1,2,4-triazolo[1,2-a]pyridazine-2-propionate of melting point 91°–92° C.

(D) 5-Carboxy-2,3,5,8-tetrahydro-1,3-dioxo-1H-1,2,4-triazolo[1,2-a]pyridazine-2-propionic acid was suspended in dry ether and the suspension was treated with a slight excess of an ethereal solution of diazomethane. The mixture was left to stand at room temperature for 2 hours, washed with 10% sodium carbonate solution, dried over magnesium sulphate and evaporated to give a residue which, after recrystallization from methanol, yielded methyl 2,3,5,8-tetrahydro-5-methoxycarbonyl-1,3-dioxo-1H-1,2,4-triazolo[1,2-a]pyridazine-2-propionate of melting point 91°–92° C.

EXAMPLE 22

Methyl 5-carboxy-2,3,5,8-tetrahydro-1,3-dioxo-1H-1,2,4-triazolo[1,2-a]pyridazine-2-propionate was dissolved in methanol and the solution was stirred at room temperature for 2 hours with 1-M sodium hydroxide solution (1.1 mol equivalents). The mixture was acidified with concentrated hydrochloric acid and then evaporated to dryness. The residue was extracted with acetonitrile and the extracts were evaporated to give 5-carboxy-2,3,5,8-tetrahydro-1,3-dioxo-1H-1,2,4- triazolo[1,2-a]pyridazine-2-propionic acid of melting point 172°–175° C. (from acetonitrile).

The following acids were prepared in an analogous manner by saponification of the corresponding esters:

(+)-5-Carboxy-2,3,5,8-tetrahydro-1,3-dioxo-1H-1,2,4-triazolo[1,2-a]pyridazine-2-propionic acid of melting point 172°–175° C. $[[\alpha]_{365}{}^{20} = +1243°$ (c=0.5 in methanol)], (−)-5-carboxy-2,3,5,8-tetrahydro-1,3-dioxo-1H-1,2,4-triazolo[1,2-a]pyridazine-2-propionic acid of melting point 172°–175° C. $[[\alpha]_{365}{}^{20} = -1245°$ (c=0.5 in methanol)], 2-(2-chloroethyl)-2,3,5,6,7,8-hexahydro-1,3-dioxo-1H-1,2,4-triazolo[1,2-a]pyridazine-5-carboxylic acid of melting point 151°–152° C., and 5-carboxy-2,3,5,6,7,8-hexahydro-1,3-dioxo-1H-1,2,4-triazolo[1,2-a]pyridazine-2-acetic acid of melting point 224°–226° C.

EXAMPLE 23

In a manner analogous to that described in Example 1(D), from methyl 3,5-dioxo-1,2,4-triazolidine-4-propionate and dimethyl hexa-2,4-dienoate, using a mixture of chloroform and dioxan as the solvent, there was obtained in 44% yield dimethyl 2-(2-methoxycarbonylethyl)-2,3,5,8-tetrahydro-1,3-dioxo-1H-1,2,4-triazolo[1,2-a]pyridazine-5,8-dicarboxylate of melting point 139°–141° C. (from methanol).

The foregoing compound was hydrolyzed in 6-M hydrochloric acid at 100° C. for 4 hours. Partial evaporation then gave in 72% yield 2-(2-carboxyethyl)-2,3,5,8-tetrahydro-1,3-dioxo-1H-1,2,4-triazolo[1,2-a]pyridazine-5,8-dicarboxylic acid in the form of a hygroscopic solid.

EXAMPLE 24

In a manner analogous to that described in Example 1(D), from 4-(2-chloroethyl)-1,2,4-triazolidine-3,5-dione and 5-phenylpenta-2,4-dienoic acid there was obtained in 75% yield cis-2-(2-chloroethyl)-2,3,5,8-tetrahydro-1,3-dioxo-8-phenyl-1H-1,2,4-triazolo[1,2-a]pyridazine-5-carboxylic acid of melting point 204°–205° C. (from acetonitrile).

EXAMPLE 25

In a manner analogous to that described in Example 1(D), from 4-(2-chloroethyl)-1,2,4-triazolidine-3,5-dione and ethyl 5-phenylpenta-2,4-dienoate there was obtained in 83% yield ethyl cis-2-(2-chloroethyl)-2,3,5,8-tetrahydro-1,3-dioxo-8-phenyl-1H-1,2,4-triazolo[1,2-a]pyridazine-5-carboxylate of melting point 130°–131° C. (from ethanol).

12.72 g (0.035 mol) of the foregoing compound and 2.87 g (0.035 mol) of anhydrous sodium acetate were heated under reflux in 100 ml of acetone for 4 hours. The acetone was removed by evaporation and the residue was partitioned between chloroform and water. The organic layer was separated, dried over magnesium sulphate and evaporated to give in 81% yield ethyl trans-2-(2-chloroethyl)-2,3,5,8-tetrahydro-1,3-dioxo-8-phenyl-1H-1,2,4-triazolo[1,2-a]pyridazine-5-carboxylate of melting point 117°–119° C. (from toluene).

The foregoing compound was hydrolyzed in 6-M hydrochloric acid at 100° C. for 4 hours. Partial evaporation than gave in 80% yield trans-2-(2-chloroethyl)-2,3,5,8-tetrahydro-1,3-dioxo-8-phenyl-1H-1,2,4-triazolo[1,2-a]pyridazine-5-carboxylic acid melting point 141°–143° C.

EXAMPLE 26

A cooled solution of 12.08 g (0.036 mol) of cis-2-(2-chloroethyl)-2,3,5,8-tetrahydro-1,3-dioxo-8-phenyl-1H-1,2,4-triazolo[1,2-a]pyridazine-5-carboxylic acid in 180 ml of methanol was treated with a solution of 2.37 g (0.036 ml) of potassium hydroxide in 15 ml of methanol. The methanol was removed by evaporation and the residue was dissolved in 150 ml of dimethyl sulphoxide. The solution was treated with 4.90 g (0.043 mol) of potassium thioacetate and the mixture was stirred at 80° C. for 20 hours. The cooled mixture was diluted with 150 ml of water, acidified with 2-M hydrochloric acid and extracted with ether. The combined extracts were dried over magnesium sulphate and evaporated to give a yellow oil which was treated with diazomethane in the usual manner. The resulting yellow oil was chromatographed on silica gel using chloroform/ethyl acetate (4:1) for the elution to give 3.8 g (27%) of methyl trans-2-(2-acetylthioethyl)-2,3,5,8-tetrahydro-1,3-dioxo-8-phenyl-1H-1,2,4-triazolo[1,2-a]pyridazine-5-carboxylate of melting point 101°–102° C. (from ethyl acetate) and 0.1 g (1%) of methyl cis-2-(2-acetylthioethyl)-2,3,5,8-tetrahydro-1,3-dioxo-8-phenyl-1H-1,2,4-triazolo[1,2-a]pridazine-5-carboxylate in the form of a colourless oil.

Methyl trans-2-(2-acetylthioethyl)-2,3,5,8-tetrahydro-1,3-dioxo-8-phenyl-1H-1,2,4-triazolo[1,2-a]pyridazine-5-carboxylate was hydrolyzed in 2-M hydrochloric acid at 100° C. for 3.5 hours. Partial evaporation then gave in 43% yield trans-2,3,5,8-tetrahydro-2-(2-mercaptoethyl)-1,3-dioxo-8-phenyl-1H-1,2,4-triazolo[1,2-a]pyridazine-5-carboxylic acid of melting point 153°–154° C.

EXAMPLE 27

(A) 4.73 g (0.013 mol) of ethyl cis-2-(2-chloroethyl)-2,3,5,8-tetrahydro-1,3-dioxo-8-phenyl-1H-1,2,4-triazolo[1,2-a]pyridazine-5-carboxylate were dissolved in 300 ml of ethanol and hydrogenated in the presence of 10% palladium-on-charcoal at room temperature. The catalyst was filtered off and the filtrate was evaporated to give 3.13 g (66%) of ethyl 2,3,5,6,7,8-hexahydro-2-(2-chloroethyl)-1,3-dioxo-8-phenyl-1H-1,2,4-triazolo[1,2-a]pyridazine-5-carboxylate of melting point 87°–89° C. (from ethanol).

(B) 3.6 g (0.01 mol) of the foregoing compound and 1.37 g (0.012 mol) of potassium thioacetate were heated under reflux in 160 ml of acetone for 30 hours. The acetone was removed by evaporation and the residue was partitioned between water and ethyl acetate. The organic layer was dried over magnesium sulphate and evaporated to give 3.5 g (85%) of ethyl 2,3,5,6,7,8-hexahydro-2-(2-acetylthioethyl)-1,3-dioxo-8-phenyl-1H-1,2,4-triazolo[1,2-a]pyridazine-5-carboxylate in the form of a yellow oil.

(C) The foregoing compound was hydrolyzed in 2-M hydrochloric acid at 100° C. for 4 hours, there being obtained in 77% yield 2,3,5,6,7,8-hexahydro-2-(2-mercaptoethyl)-1,3-dioxo-8-phenyl-1H-1,2,4-triazolo[1,2-a]pyridazine-5-carboxylic acid of melting point 172°–175° C.

EXAMPLE 28

In a manner analogous to that described in Example 1(D), from 4-(2-chloroethyl)-1,2,4-triazolidine-3,5-dione and ethyl 5-(4-chlorophenyl)penta-2,4-dienoate there was obtained in 85% yield ethyl 2-(2-chloroethyl)-2,3,5,8-tetrahydro-8-(4-chlorophenyl)-1,3-dioxo-1H-1,2,4-triazolo[1,2-a]pyridazine-5-carboxylate of melting point 126°–127° C. (from chloroform).

The foregoing compound was hydrogenated in a manner analogous to that described in Example 26(A) to give an 80% yield of ethyl 2-(2-chloroethyl)-2,3,5,6,7,8-hexahydro-8-(4-chlorophenyl)-1,3-dioxo-1H-1,2,4-triazolo[1,2-a]pyridazine-5-carboxylate of melting point 111°–112° C. (from ethanol).

The foregoing compound was treated with potassium thioacetate in a manner analogous to that described in Example 26(B) to give a 46% yield of ethyl 2-(2-acetylthioethyl)-2,3,5,6,7,8-hexahydro-8-(4-chlorophenyl)-1,3-dioxo-1H-1,2,4-triazolo[1,2-a]pyridazine-5-carboxylate in the form of a pale yellow oil.

Hydrolysis of the foregoing compound in 2-M hydrochloric acid at 100° C. for 12 hours gave an 80% yield of 8-(4-chlorophenyl)-2,3,5,6,7,8-hexahydro-2-(2-mercaptoethyl)-1,3-dioxo-1H-1,2,4-triazolo[1,2-a]pyridazine-5-carboxylic acid of melting point 189°–190° C.

EXAMPLE 29

In a manner analogous to that described in Example 1(D), from 4-(2-chloroethyl)-1,2,4-triazolidine-3,5-dione and ethyl 5-(4-methoxyphenyl)penta-2,4-dienoate there was obtained in 70% yield ethyl cis-2-(2-chloroethyl)-2,3,5,8-tetrahydro-8-(4-methoxyphenyl)-1,3-dioxo-1H-1,2,4-triazolo[1,2-a]pyridazine-5-carboxylate of melting point 110°–112° C. (from ethanol).

The foregoing compound was hydrolyzed in 6-M hydrochloric acid at 100° C. for 10 hours to give in 30% yield cis-2-(2-chloroethyl)-2,3,5,8-tetrahydro-8-(4-methoxyphenyl)-1,3-dioxo-1H-1,2,4-triazolo[1,2-a]pyridazine-5-carboxylic acid of melting point 158°–161° C. (from ethyl acetate/hexane).

EXAMPLE 30

In a manner analogous to that described in Example 1(D), from 4-(2-chloroethyl)-1,2,4-triazolidine-3,5-dione and ethyl 5-(4-nitrophenyl)penta-2,4-dienoate there was obtained in 75% yield ethyl cis-2-(2-chloroethyl)-2,3,5,8-tetrahydro-8-(4-nitrophenyl)-1,3-dioxo-1H-1,2,4-triazolo[1,2-a]pyridazine-5-carboxylate of melting point 142°–143° C. (from toluene).

Hydrolysis of the foregoing compound in 6-M hydrochloric acid at 100° C. for 12 hours gave in 34% yield cis-2-(2-chloroethyl)-2,3,5,8-tetrahydro-8-(4-nitrophenyl)-1,3-dioxo-1H-1,2,4-triazolo[1,2-a]pyridazine-5-carboxylic acid of melting point 192°–194° C. (from ethyl acetate).

EXAMPLE 31

In a manner analogous to that described in Example 1(D), from 1,2,4-triazolidine-3,5-dione and ethyl 5-phenylpenta-2,4-dienoate there was obtained in 81% yield ethyl 2,3,5,8-tetrahydro-1,3-dioxo-8-phenyl-1H-1,2,4-triazolo[1,2-a]pyridazine-5-carboxylate of melting point 196°–197° C. (from ethanol).

The foregoing compound was treated with formaldehyde in a manner analogous to that described in Example 18 to give a 60% yield of ethyl 2-hydroxymethyl-2,3,5,8-tetrahydro-1,3-dioxo-8-phenyl-1H-1,2,4-triazolo[1,2-a]pyridazine-5-carboxylate of melting point 129°–133° C. (from ethyl acetate/hexane).

In a manner analogous to that described in Example 18, the foregoing compound was reacted with phosphorus pentachloride to give, in 73% yield, ethyl 2-chloromethyl-2,3,5,8-tetrahydro-1,3-dioxo-8-phenyl-1H-1,2,4-triazolo[1,2-a]pyridazine-5-carboxylate of melting point 145°–146° C. (from ethyl acetate).

The foregoing compound was hydrogenated in a manner analogous to that described in Example 26(A) to give in 64% yield ethyl 2-chloromethyl-2,3,5,6,7,8-hexahydro-1,3-dioxo-8-phenyl-1H-1,2,4-triazolo[1,2-a]pyridazine-5-carboxylate of melting point 104°–106° (from ethyl acetate/hexane).

In a manner analogous to that described in Example 10, the foregoing compound was reacted with potassium thioacetate to give in 80% yield ethyl 2-acetylthiomethyl-2,3,5,6,7,8-hexahydro-1,3-dioxo-8-phenyl-1H-1,2,4-triazolo[1,2-a]pyridazine-5-carboxylate in the form of a pale yellow oil.

The foregoing compound was hydrolyzed in 2-M hydrochloric acid at 100° C. for 2.5 hours. Partial evaporation then gave in 81% yield 2,3,5,6,7,8-hexahydro-2-mercaptomethyl-1,3-dioxo-8-phenyl-1H-1,2,4-triazolo[1,2-a]-pyridazine-5-carboxylic acid of melting point 85°–86° C. (decomposition).

EXAMPLE 32

440 mg of methyl 2-acetylthiomethyl-2,3,5,8-tetrahydro-1,3-dioxo-1H-1,2,4-triazolo[1,2-a]pyridazine-5-carboxylate, prepared as described in Example 10, were stirred in a mixture of 3 ml of methanol and 1-M sodium hydroxide at 20° C. for 2 hours under nitrogen. The solution obtained was acidified, saturated with sodium chloride and extracted with chloroform. The chloroform extracts were dried over magnesium sulphate and evaporated to give, after recrystallization from ethyl acetate/hexane, 220 mg (62%) of 2,4,5,8-tetrahydro-2-mercaptomethyl-1,3-dioxo-1H-1,2,4-triazolo[1,2-a]pyridazine-5-carboxylic acid of melting point 185°–187° C.

EXAMPLE 33

In a manner analogous to that described in Example 10, from methyl 2,3,5,8-tetrahydro-2-(3-chloropropyl)-1,3-dioxo-1H-1,2,4-triazolo[1,2-a]pyridazine-5-carboxylate there was obtained in 48% yield methyl 2,3,5,8-tetrahydro-2-(3-acetylthiopropyl)-1,3-dioxo-1H-1,2,4-triazolo[1,2-a]pyridazine-5-carboxylate in the form of an oil.

In a manner analogous to that described in Example 32, from methyl 2,3,5,8-tetrahydro-2-(3-acetylthiopropyl)-1,3-dioxo-1H-1,2,4-triazolo[1,2-a]pyridazine-5-carboxylate there was obtained in 35% yield 2,3,5,8-tetrahydro-2-(3-mercaptopropyl)-1,3-dioxo-1H-1,2,4-triazolo[1,2-a]pyridazine-5-carboxylic acid of melting point 119°–121° C. (from ethyl acetate/hexane).

EXAMPLE 34

In a manner analogous to that described in Example 16, methyl 2-chloromethyl-2,3,5,8-tetrahydro-1,3-dioxo-1H-1,2,4-triazolo[1,2-a]pyridazine-5-carboxylate, prepared as described in Example 18, was converted into methyl 2-chloromethyl-2,3,5,6,7,8-hexahydro-1,3-dioxo-1H-1,2,4-triazolo(1,2-a)pyridazine-5-carboxylate of melting point 125°–127° C.

In a manner analogous to that described in Example 10, from methyl 2-chloromethyl-2,3,5,6,7,8-hexahydro-1,3-dioxo-1H-1,2,4-triazolo[1,2-a]pyridazine-5-carboxylate there was obtained in 37% yield methyl 2-acetylthiomethyl-2,3,5,6,7,8-hexahydro-1,3-dioxo-1H-1,2,4-triazolo[1,2-a]pyridazine-5-carboxylate of melting point 100°–102° C. (from ethyl acetate/hexane).

In a manner analogous to that described in Example 32, from methyl 2-acetylthiomethyl-2,3,5,6,7,8-hexahydro-1,3-dioxo-1H-1,2,4-triazolo[1,2-a]pyridazine-5-carboxylate there was obtained in 29% yield 2,3,5,6,7,8-hexahydro-2-mercaptomethyl-1,3-dioxo-1H-1,2,4-triazolo[1,2-a]pyridazine-5-carboxylic acid of melting point 157.5°–158.5° C. (from ethyl acetate/hexane).

The following Examples illustrate pharmaceutical preparations containing the triazolopyridazine derivatives provided by the present invention:

EXAMPLE A

Tablets containing the following ingredients are produced in a conventional manner:

| Ingredient | Per tablet |
| --- | --- |
| Triazolopyridazine derivative | 10.0 mg |
| Lactose | 125.0 mg |
| Maize starch | 75.0 mg |
| Talc | 4.0 mg |
| Magnesium stearate | 1.0 mg |
| Total weight | 215.0 mg |

EXAMPLE B

Capsules containing the following ingredients are produced in a conventional manner:

| Ingredient | Per capsule |
| --- | --- |
| Triazolopyridazine derivative | 25.0 mg |
| Lactose | 150.0 mg |
| Maize starch | 20.0 mg |
| Talc | 5.0 mg |
| Total weight | 200.0 mg |

What is claimed is:

1. A triazolopyridazine derivative of the formula:

$$R^1-A-N\overset{O}{\underset{O}{\diagdown}}N\overset{R^5}{\underset{N}{\diagdown}}\overset{R^4}{\underset{R^3}{=}}COR^2$$

wherein A is methylene, ethylene or propylene which may be substituted by lower alkyl; $R^1$ is halogen, carboxyl, lower alkoxycarbonyl, aminocarbonyl, hydroxyaminocarbonyl, hydrazinocarbonyl, mercapto, lower alkanoylthio or aryl-lower alkylthio; $R^2$ is hydroxy, lower alkoxy or amino; $R^3$ and $R^4$ each is hydrogen or halogen or $R^3$ is hydrogen and $R^4$ is hydroxy; and $R^5$ is hydrogen, lower alkyl, aryl, carboxy, lower alkoxycarbonyl or aminocarbonyl; and the broken line denotes an optional carbon-carbon bond which can be present only when $R^3$ and $R^4$ each is hydrogen, or a salt of an acid of formula I with a pharmaceutically acceptable base.

2. The compound of claim 1 which is 5-carboxy-2,3,5,6,7,8-hexahydro-1,3-dioxo-1H-1,2,4-triazolo[1,2-a]pyridazine-2-acetic acid.

3. The compound of claim 1 which is methyl 2,3,5,6,7,8-hexahydro-1,3-dioxo-1H-1,2,4-triazolo[1,2-a]pyridazine-2-propionate.

4. The compound of claim 1 which is 2-(2-chloroethyl)-2,3,5,6,7,8-hexahydro-1,3-dioxo-1H-1,2,4-triazolo[1,2-a]pyridazine-5-carboxylic acid.

5. The compound of claim 1 which is methyl 2-(2-chloroethyl)-2,3,5,6,7,8-hexahydro-1,3-dioxo-1H-1,2,4-triazolo[1,2-a]pyridazine-5-carboxylate.

6. The compound of claim 1 which is 2,3,5,6,7,8-hexahydro-2-(2-mercaptoethyl)-1,3-dioxo-8-phenyl-1H-1,2,4-triazolo[1,2-a]pyridazine-5-carboxylic acid.

7. Triazolopyridazine derivatives of claim 1 wherein a double bond is present in the 6,7-position.

8. The compound of claim 7 which is methyl 2,3,5,8-tetrahydro-2-(3-acetylthiopropyl)-1,3-dioxo-1H-1,2,4-triazolo[1,2-a]pyridazine-5-carboxylate.

9. The compound of claim 7 which is methyl 5-carboxy-2,3,5,8-tetrahydro-1,3-dioxo-1H-1,2,4-triazolo[1,2-a]pyridazine-2-propionate.

10. The compound of claim 7 which is 2-(2-benzylthioethyl)-2,3,5,8-tetrahydro-1,3-dioxo-1H-1,2,4-triazolo[1,2-a]pyridazine-5-carboxylic acid.

11. The compound of claim 7 which is methyl 2-acetylthiomethyl-2,3,5,8-tetrahydro-1,3-dioxo-1H-1,2,4-triazolo[1,2-a]pyridazine-5-carboxylate.

12. The compound of claim 7 which is 2-(3-chloropropyl)-2,3,5,8-tetrahydro-1,3-dioxo-1H-1,2,4-triazolo[1,2-a]pyridazine-5-carboxylic acid.

13. Triazolopyridazine derivatives of claim 7 wherein $R^2$ is hydroxy.

14. Triazolopyridazine derivatives of claim 13 wherein $R^1$ is carboxyl, hydroxyaminocarbonyl or mercapto.

15. The compound of claim 14 which is 5-carboxy-2,3,5,8-tetrahydro-1,3-dioxo-1H-1,2,4-triazolo[1,2-a]pyridazine-2-butyric acid.

16. The compound of claim 14 which is 5-carboxy-2,3,5,8-tetrahydro-8-methyl-1,3-dioxo-1H-1,2,4-triazolo[1,2-a]pyridazine-2-propionic acid.

17. The compound of claim 14 which is 2,3,5,8-tetrahydro-2-mercaptomethyl-1,3-dioxo-1H-1,2,4,-triazolo[1,2-a]pyridazine-5-carboxylic acid.

18. The compound of claim 14 which is 5-carboxy-2,3,5,8-tetrahydro-1,3-dioxo-1H-1,2,4-triazolo[1,2-a]pyridazine-2-propionic acid.

19. The compound of claim 14 which is 5-carboxy-2,3,5,8-tetrahydro-8-phenyl-1,3-dioxo-1H-1,2,4-triazolo[1,2-a]pyridazine-2-propionic acid.

20. Triazolopyridazine derivatives of claim 14 wherein A is ethylene.

21. A compound of the formula $$HN\overset{O}{\underset{O}{\diagdown}}N\overset{R^5}{\underset{N}{\diagdown}}\overset{R^4}{\underset{R^3}{=}}COR^2$$

wherein $R^2$ is hydroxy, lower alkoxy or amino; $R^3$ and $R^4$ each is hydrogen or halogen, or $R^3$ is hydrogen and $R^4$ is hydroxy; and $R^5$ is hydrogen or lower alkyl, aryl, carboxy, lower alkoxycarbonyl or aminocarbonyl; and the broken line denotes an optional carbon-carbon bond which can be present only when $R^3$ and $R^4$ each is hydrogen, with the proviso that when a double bond is present in the 6,7-position and $R^2$ is hydroxy, or when $R^3$ and $R^4$ each is hydrogen and $R^2$ is hydroxy, $R^5$ is other than hydrogen.

22. The compound of claim 20 which is trans-2,3,5,8-tetrahydro-2-(2-mercaptoethyl)-1,3-dioxo-8-phenyl-1H-1,2,4-triazolo[1,2-a]pyridazine-5-carboxylic acid.

23. The compound of claim 20 which is cis 2-(2-chloroethyl)-2,3,5,8-tetrahydro-8-(4-methoxyphenyl)-1,3-dioxo-1H-1,2,4-triazolo[1,2-a]pyridazine-5-carboxylic acid.

24. The compound of claim 20 which is cis-2-(2-chloroethyl)-2,3,5,8-tetrahydro-8-(4-nitrophenyl)-1,3-dioxo-1H-1,2,4-triazolo[1,2-a]pyridazine-5-carboxylic acid.

25. The compound of claim 20 which is 2,3,5,8-tetrahydro-2-(2-mercaptoethyl)-1,3-dioxo-1H-1,2,4-triazolo[1,2-a]pyridazine-5-carboxylic acid.

26. The compound of claim 20 which is 2-[2-(N-hydroxycarbamoyl)ethyl]-2,3,5,8-tetrahydro-1,3-dioxo-1H-1,2,4-triazolo[1,2-a]pyridazine-5-carboxylic acid.

27. The compound of claim 20 which is 2-(2-carbamoylethyl)-2,3,5,8-tetrahydro-1,3-dioxo-1H-1,2,4-triazolo[1,2-a]pyridazine-5-carboxylic acid.

28. An antihypertensive composition which comprises effective amounts of a triazolopyridazine derivative of the formula

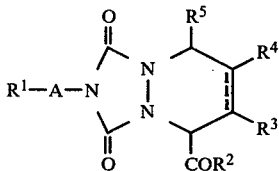

wherein A is methylene, ethylene or propylene which may be substituted by lower alkyl; $R^1$ is halogen, carboxyl, lower alkoxycarbonyl, aminocarbonyl, hydroxyaminocarbonyl, hydrazinocarbonyl, mercapto, lower alkanoylthio or aryl-lower alkylthio; $R^2$ is hydroxy, lower alkoxy or amino; $R^3$ and $R^4$ each is hydrogen or halogen or $R^3$ is hydrogen and $R^4$ is hydroxy; and $R^5$ is hydrogen, lower alkyl, aryl, carboxy, lower alkoxycarbonyl or aminocarbonyl; and the broken line denotes an optional carbon-carbon bond which can be present only when $R^3$ and $R^4$ each is hydrogen, or a pharmaceutically-acceptable salt of an acid thereof and a pharmaceutically-acceptable carrier.

29. An antihypertensive composition according to claim 21 wherein A is ethylene; $R^1$ is carboxy, hydroxyaminocarbonyl or mercapto; $R^2$ is hydroxy; $R^3$ and $R^4$ each is hydrogen; $R^5$ is lower alkyl, aryl, carboxy, lower alkoxycarbonyl or aminocarbonyl and a double bond is present in the 6,7-position, or a pharmaceutically-acceptable salt of an acid thereof and a pharmaceutically-acceptable carrier.

30. Compounds of the general formula

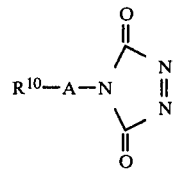

Formula II wherein A is methylene, ethylene or propylene which may be substituted by lower alkyl; and $R^{10}$ is halogen, carboxyl or lower alkoxycarbonyl.

31. Compounds of the general formula

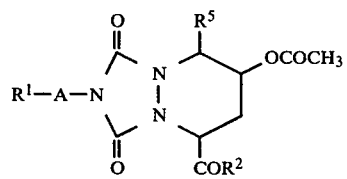

Formula XI wherein A is methylene, ethylene or propylene which may be substituted by lower alkyl; $R^1$ is halogen, carboxyl, lower alkoxycarbonyl, aminocarbonyl, hydroxyaminocarbonyl, hydrazinocarbonyl, mercapto, lower alkanoylthio or aryl-lower alkylthio; $R^2$ is hydroxy, lower alkoxy or amino; $R^3$ and $R^4$ each is hydrogen or halogen or $R^3$ is hydrogen and $R^4$ is hydroxy; $R^5$ is hydrogen, lower alkyl, aryl, carboxy, lower alkoxycarbonyl or aminocarbonyl; and the broken line denotes an optional carbon-carbon bond which can be present only when $R^3$ and $R^4$ each is hydrogen.

32. Compounds of the general formula

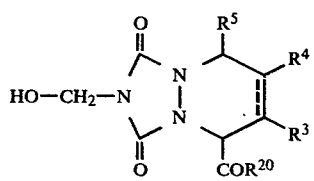

Formula VIII wherein $R^2$ is hydroxy, lower alkoxy or amino; $R^3$ and $R^4$ each is hydrogen or halogen or $R^3$ is hydrogen and $R^4$ is hydroxy; and $R^5$ is hydrogen, lower alkyl, aryl, carboxy, lower alkoxycarbonyl or aminocarbonyl; and the broken line denotes an optional carbon-carbon bond which can be present only when $R^3$ and $R^4$ each is hydrogen.

* * * * *